United States Patent [19]

Davis, Jr.

[11] 4,144,032
[45] Mar. 13, 1979

[54] PERSONAL DOSIMETER AND METHOD OF USE

[76] Inventor: Frank R. Davis, Jr., 12 S. Mountain Ave., Montclair, N.J. 07042

[21] Appl. No.: 827,349

[22] Filed: Aug. 24, 1977

[51] Int. Cl.² ............................................. G01N 31/06
[52] U.S. Cl. .............................. 23/232 R; 73/421.5 R; 422/58; 422/88
[58] Field of Search ............. 23/254 R, 232 R; 73/23, 73/421.5 R

[56] References Cited
U.S. PATENT DOCUMENTS

| | | | |
|---|---|---|---|
| 3,397,965 | 8/1968 | Berueffy | 23/254 RX |
| 3,482,944 | 12/1969 | Plantz et al. | 23/254 R |
| 3,681,027 | 8/1972 | Smith | 23/254 R X |
| 3,985,017 | 10/1976 | Goldsmith | 73/23 |
| 3,992,153 | 11/1976 | Ferber | 23/254 R X |

Primary Examiner—Morris O. Wolk
Assistant Examiner—Arnold Turk
Attorney, Agent, or Firm—Kenyon & Kenyon, Reilly, Carr & Chapin

[57] ABSTRACT

Personal dosimeter, which provides great ease in immediately obtaining reading results, includes a plastic tube, open on the bottom, and containing near its top, a well through the bottom of which is inserted a piece of inert wick and a cover made of a soft plastic placed over the top of the tube. When the dosimeter is to be put into use, a predetermined amount of liquid reagent is injected into the well formed near the top, which reactant moves by capillary action into the inert wick where it adsorbs, absorbs or reacts with a toxic substance to be measured by the dosimeter. After the required time period for measuring exposure, the dosimeter is turned over, additional reactant placed in the tube from the bottom and mixed with the reactant therein, the reactant then being used to determine the concentration of the toxic substance.

15 Claims, 1 Drawing Figure

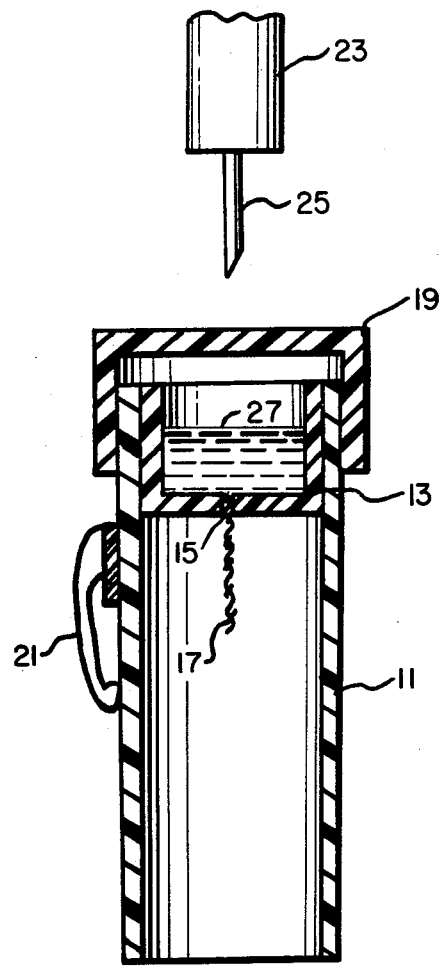

PERSONAL DOSIMETER AND METHOD OF USE

BACKGROUND OF THE INVENTION

This invention relates to personal dosimeters in general and more particularly to an improved personal dosimeter which is of extremely simple design and which can be produced at low cost.

Over the recent years, there has been increasing concern regarding the exposure of workers to harmful substances. This has resulted in the enactment of various laws at the Federal and State levels relating to occupational health and safety. As a result, requirements are placed on facilities where harmful substances are present to monitor the exposure of their workers to these substances.

One of the typical manners of determining the presence of harmful substances has been to use a pump to draw a sample of the ambient air containing the toxic substance through a material which will absorb or adsorb the toxic substance and then extract the toxic substance therefrom and measure its concentration using a chromatograph or the like. For example, to detect the time weighted average of hydrocarbons, a tube filled with carbon has been used as a collecting medium. A pump draws the sample through the carbon where the toxic substance to be measured is trapped. Later, the toxic substance is dissolved out of the carbon and injected into a chromatograph and read in PPM. This is an expensive method, particularly because of the high cost of pumps. Further information concerning the sampling and analysis is found in an article entitled, "A Convenient Optimized Method For The Analysis Of Selected Solvent Vapors In the Industrial Atmosphere" by White et al. published in *The American Industrial Hygiene Association Journal*, vol. 31, March-April, 1970.

Because of the difficulties and high costs of using the aforementioned method of sampling, there have been attempts to develop a personal dosimeter. Such is disclosed, for example, in U.S. Pat. No. 3,985,017. The dosimeter disclosed therein, which is termed a Gaseous Contaminant Personal Dosimeter comprises a container, an inert porous thin barrier element forming one side of the container with the barrier element adapted to permit diffusion of the gaseous contaminants that are to be determined into the interior of the containers and a gaseous contaminant collecting medium within the container and positioned opposite the barrier element to collect the gaseous contaminant diffused from the ambient atomsphere through the barrier element. It also includes means to inhibit convection movement of the diffused gases within the container and permits the determination of gaseous contaminants in proportion to ambient concentrations independent of ambient convection patterns. Although shown as a cylindrical device in the patent, the actual device, which is sold under the trade name Gasbadge by the Walton division of Abcor, Inc. of Wilmington, Mass., is in a rectangular shape, quite similar to the shape of conventional radiation dosimeters. The dosimeter actually being produced includes a back containing a spring clip into which the collecting medium is placed, an open grid placed thereover to define diffusion geometry, a draft shield made from non-reactive porous material, a badge front with an opening to allow diffusion of gas vapors into the device and a removable protective cover. Obviously, this is a relatively expensive device, even though it is possible to replace the collection material therein.

One serious problem with the dosimeter of the aforementioned U.S. Patent is that the analysis of results are preferably carried out in a laboratory. Because of the fact that, in essence, the materials which are used to adsorb, absorb or react must be solids, it is necessary to go through a chemical analysis which is comparatively complex in order to obtain the necessary information concerning concentrations of the toxic gas in the ambient air.

There exist in the art, many collection solutions or reagents which change color depending on the concentration of a toxic substance in the solution. Quite often, the solution is a water based solution and large fields of analysis have been built around water analysis and resulting color changes with absorption. In some cases, a water sample is taken and the proper reagent added to the water. The reagent results in color depending on the concentration of the substance therein and a color comparator is then used to determine the concentration, i.e., the actual color is compared with colors relating to predetermined known concentrations. Alternatively, color measurements can be done using other types of colorimeters such as a color photometer.

In line with this, it has been common to take a collection solution and place it in an impinger. The ambient air to be measured is then drawn through the impinger by a pump with the substance under consideration absorbed into the solution which then changes color as a result. After the sample has been collected, some of the solution is poured into a cuvette and placed in an axial reader to determine the closest color match with the comparator index number. Alternatively, the color comparison can be done on a color photometer.

This gives immediate results without complicated chemical analysis. However, it does depend on the availability of a collecting solution. Attempts to use a solution in a personal dosimeter heretofore have not been successful because the solution tended to dry before the measurement time period, which might be eight hours or more, was up.

Thus, there is a need for an improved dosimeter which can use solutions, particularly solutions which indicate concentrations by color changes, to measure the amount of harmful substances, e.g., toxic gases, in the ambient air.

SUMMARY OF THE INVENTION

The present invention provides a solution to this problem. This is accomplished by providing a plastic tube which is open on the bottom and which contains near its top a well. The well contains a slit therein through which slit is fastened an inert wick. A cover of flexible plastic is placed over the top to close off the well area. When it is desired to begin sampling, a predetermined amount of collecting solution is injected into the well through the flexible plastic cover. The solution wicks down and keeps the wick wet for over eight hours. At the end of the typical eight hour working period, for which the dosimeter is worn, the dosimeter is turned upside down and additional collection solution poured therein and mixed with the solution which has collected the toxic substance. This solution is then analyzed. Preferably, it is analyzed by being poured into a cuvette and analyzed by color change in the same manner as has been done in the prior art. However, other analysis techniques, such as changes in conductivity, pH, etc. can also be used. With specific respect to the ability to take accurate samples using a tubular dosimeter, reference should be had to the article "Personal Sampler For Nitrogen Dioxide" by E. D. Palmes et al. published in *The American Industrial Hygiene Association Journal*, volume 37 October 1976.

BRIEF DESCRIPTION OF THE DRAWINGS

The single FIGURE is a cross section through the dosimeter of the present invention.

DETAILED DESCRIPTION OF THE INVENTION

FIG. 1 is a cross sectional view of the dosimeter of the present invention. The dosimeter is made up of plastic tube 11. For example, this may be commercial acrylic tubing ½" O.D., ⅜" I.D., with a length of 2½ to 3 inches. At the upper end of the tube 11 there is inserted a plastic well member 13 which forms a well. Essentially, this may be formed of a typical tube cap, or cover, of smaller diameter than the cap or cover 19 which is placed over the top of the tube 11, made of any plastic material, as will be further explained below. An example is a cap made of low density polyethylene such as what are known as Caplugs obtainable from Protective Closures Co., Inc., Buffalo, N.Y. The well member 13 contains a slit 15 in its center in which is inserted an inert wick 17 preferably made of glass paper 17. This glass paper is of the type normally used as filter paper and is obtainable, for example, from the Whatman Co. of Clifton, N.J. In essence, any material which will absorb a liquid, which exhibits capillary properties and is relatively inert, is useful as a wick 17.

Placed over the end of the tube containing the well is a cap 19 which again may be the type of cap described above made of low density polyethylene. A conventional pocket clip 21 is placed around the tube 11 to permit the tube to be clipped to a wearer's pocket.

What is described so far, is a manner in which the dosimeter exists prior to use. When it is desired to use the dosimeter, a hypodermic syringe 23 having a needle 25 and containing a predetermined amount of collection fluid is inserted through the cap 19 and the collection fluid 27 discharged into the well 13. The collection fluid then wicks down into the wick 17. If desired, the cap can be placed on the tube so that its top is not in abutment with the top of the tube. When put into use, pressing down on the cap will apply additional pressure to the fluid 27 resulting in it more quickly wicking into the wick 17.

The dosimeter is then worn by a person who is being exposed to a toxic gas for a predetermined period of time, for example, for his eight hour work shift. At the end of his shift, the dosimeter is removed and turned upside down. Additional collection fluid is placed therein, an additional cap, such as the cap 19, can be placed over the bottom, a shaking action carried out to mix the collection solution just added with the solution with absorbed toxic substance found on the wick 17 and the solution then analyzed such as being poured into a cuvette for analysis by conventional color techniques.

Thereafter, the dosimeter can be washed out with an appropriate cleansing solution, allowed to dry and be ready for additional use.

In addition to color techniques, other methods of analysis may be used with the dosimeter of the present invention such as changes in pH, changes in conductivity and so forth. In general, any analysis system which relies on toxic substances being absorbed or adsorbed into a solution or which will react with a solution, can be used with the dosimeter of the present invention. Examples of reagents or collecting solutions and the substances which can be measured are given below.

| TOXIC GAS | SOLUTION | ANALYSIS |
|---|---|---|
| Acetic acid | Glycerol-water with methyl purple indicator | Color or pH |
| Butylamine | Ninhydrin 1,2,3, Triketchydrindene | Color (purple) |
| Carbon Disulfide | Diethylemine and copper acetate | Color (yellow) |
| Chlorine | 0.0125N to 0.10N Sodium hydroxide | Color (yellow) |
| Methyl Alcohol | distilled water: 3% potassium permangante Shiffs reagent | Color |

Additional information with respect to these tests and others is available from the Analytical Abstracts of the American Industrial Hygiene Association.

I claim:

1. An improved personal dosimeter comprising:
   (a) an elongated plastic tube open on both ends;
   (b) a well formed at one end of said tube;
   (c) a wick extending into said well from the other end of said tube; and
   (d) a cover over said one end of said tube containing said well whereby a solution which adsorbs, absorbs or reacts with a toxic gas in the air may be placed in said well when it is desired to use the said dosimeter and will wick from said well into said wick, the other end of said tube being open to the ambient air and permitting a transfer thereof to said wick.

2. The dosimeter of claim 1 wherein said wick is made of glass paper.

3. The dosimeter of claim 1 wherein said tube is made of acrylic tubing and said cap of low density polyethylene.

4. The dosimeter of claim 1 wherein said well comprises an inverted tube cover of smaller diameter disposed in said tube.

5. A method of constructing a personal dosimeter comprising:
   (a) obtaining an elongated piece of plastic tubing;
   (b) forming a well at one end of said plastic tubing;
   (c) forming a slit in the bottom of said well;
   (d) inserting an inert wick in said slit so as to extend from said well toward the other end of said tube; and
   (e) placing a cover over said one end of said tube containing said well.

6. The method of claim 5 wherein said tube is made of acrylic plastic and said cover of low density polyethylene.

7. The method of claim 5 wherein the step of forming said well comprises inserting an inverted tube cover of smaller diameter inside one end of said tube.

8. A method of sampling the exposure of a person to a toxic gas utilizing a personal dosimeter comprising an elongated plastic tube open on both ends, a well formed at one end of the tube, a wick extending into the well from the other end of the tube, and a cover disposed over said one end of said tube containing said well comprising:

injecting a predetermined amount of a collecting solution into said well, through said cover with a hypodermic syringe, just prior to use by the person whose exposure to a toxic gas is to be measured and then disposing the dosimeter on the person whose exposure is to be measured.

9. The method according to claim 8 wherein said cover is disposed on said tube such that its top does not abut against the end of said tube and further including the step of pressing down on said cover after injecting said liquid to aid in the wicking of said liquid into said wick.

10. The method according to claim 8 and further including the step of, after exposure, pouring an additional amount of collecting fluid into the open end of said tube, mixing said additional collection solution with the collecting solution then on said wick; and analyzing said collecting solution.

11. The method according to claim 10 wherein said step of analyzing comprises measuring the conductivity of said collecting solution to determine a change in conductivity.

12. The method according to claim 10 wherein said step of analyzing comprises measuring the pH of said collecting solution.

13. The method according to claim 10 wherein said collecting solution is a solution which changes color upon absorbing, adsorbing or reacting with said toxic gas and wherein said step of analyzing comprises analyzing the color of said collecting solution.

14. The method according to claim 13 wherein said step of analyzing comprises analyzing the color of said collecting solution in an axial reader.

15. The method according to claim 13 wherein said step of analyzing comprises analyzing the color of said collecting solution in a color photometer.

* * * * *